US009522224B2

(12) United States Patent
Borges et al.

(10) Patent No.: US 9,522,224 B2
(45) Date of Patent: Dec. 20, 2016

(54) INDUCTIVELY POWERED MODULAR MEDICAL DEVICE SYSTEM

(71) Applicant: CareFusion 303, Inc., San Diego, CA (US)

(72) Inventors: Gregory Borges, San Diego, CA (US); Thomas John Carlisle, San Diego, CA (US); Chris Clarke, San Diego, CA (US); Pascal Daniel, San Diego, CA (US); David George Fern, San Diego, CA (US); Timothy Charles Frearson, San Diego, CA (US); Igor V. Nesterenko, San Diego, CA (US); Stephen Daniel Roberts, San Diego, CA (US); Daniel Hans Vik, San Diego, CA (US); James Patrick Wilkinson, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 689 days.

(21) Appl. No.: 13/829,744

(22) Filed: Mar. 14, 2013

(65) Prior Publication Data

US 2014/0276426 A1 Sep. 18, 2014

(51) Int. Cl.
*A61M 5/142* (2006.01)
*A61M 5/14* (2006.01)

(52) U.S. Cl.
CPC ........... *A61M 5/142* (2013.01); *A61M 5/1413* (2013.01); *A61M 5/1415* (2013.01); *A61M 2205/35* (2013.01); *A61M 2205/3569* (2013.01); *A61M 2205/6045* (2013.01)

(58) Field of Classification Search
CPC .. A61M 5/142; A61M 5/1415; A61M 5/1413; A61M 2205/35; A61M 2205/6045; A61M 2205/3569
USPC ........................................................ 307/104
See application file for complete search history.

(56) References Cited

U.S. PATENT DOCUMENTS 4,756,706 A 7/1988 Kerns et al.
4,898,578 A 2/1990 Rubalcaba, Jr.
5,782,805 A 7/1998 Meinzer et al.
5,954,527 A 9/1999 Jhuboo et al.
6,165,149 A 12/2000 Utterberg et al.
6,593,528 B2 * 7/2003 Franklin-Lees ..... A61M 5/1413 174/50
6,752,787 B1 6/2004 Causey, III et al.
(Continued)

FOREIGN PATENT DOCUMENTS

EP 1684396 A2 7/2006
EP 2560116 A2 2/2013
(Continued)

*Primary Examiner* — Jared Fureman
*Assistant Examiner* — Michael Warmflash
(74) *Attorney, Agent, or Firm* — Mintz Levin Cohn Ferris Glovsky and Popeo, P.C.

(57) ABSTRACT

A system includes an inductive backplane, at least one communications interface, and a control unit. The inductive backplane is configured to secure and inductively power a plurality of detachable medical device modules. The control unit controls, via the at least one communications interface, at least one attribute of each medical device module when the medical device module is secured to the inductive backplane. Related apparatus, systems, techniques and articles are also described.

26 Claims, 10 Drawing Sheets

110
130
220
210
222
224
150A
150B
150C
150D
200

(56) References Cited

U.S. PATENT DOCUMENTS 7,150,735 B2 12/2006 Hickle
7,316,648 B2 1/2008 Kelly et al.
7,553,291 B2 6/2009 Duffy et al.
7,713,240 B2 * 5/2010 Istoc ..................... A61M 5/142 604/131
7,884,735 B2 * 2/2011 Newkirk ................ A61G 7/012 211/26
7,933,780 B2 * 4/2011 De La Huerga .. A61M 5/14212 235/375
7,978,564 B2 * 7/2011 De La Huerga .. A61M 5/14212 221/15
8,118,778 B2 2/2012 Haylor et al.
8,224,481 B2 7/2012 Bylsma et al.
8,310,468 B2 * 11/2012 Martin ................... F16M 11/10 248/274.1
8,353,288 B2 1/2013 Schermeier et al.
2002/0147425 A1 10/2002 Briggs et al.
2005/0033124 A1 * 2/2005 Kelly .................. G06F 19/3418 600/300
2006/0241356 A1 * 10/2006 Flaherty ................... A61B 5/04 600/301
2007/0156089 A1 7/2007 Yu
2007/0219495 A1 9/2007 Kato et al.
2008/0045904 A1 2/2008 Estes et al.
2008/0079392 A1 * 4/2008 Baarman ............... H02J 7/0072 320/108
2008/0269716 A1 10/2008 Bonde et al.
2008/0287763 A1 * 11/2008 Hayter ................. A61B 5/0002 600/365
2009/0106567 A1 * 4/2009 Baarman ............... G06F 1/1628 713/300
2009/0115199 A1 5/2009 Dale
2009/0306592 A1 12/2009 Kasai et al.
2011/0178462 A1 * 7/2011 Moberg ............... A61B 5/0002 604/151
2012/0078218 A1 * 3/2012 Barnes ................ A61M 5/1413 604/500
2012/0191059 A1 7/2012 Cummings et al.
2012/0312196 A1 * 12/2012 Newkirk ................ H02J 7/025 108/23
2013/0046871 A1 * 2/2013 Vik ....................... G06F 15/173 709/223
2013/0092728 A1 * 4/2013 Vik ........................ G06Q 50/22 235/375
2014/0265611 A1 9/2014 Fern et al.
2014/0276424 A1 9/2014 Davis et al.

FOREIGN PATENT DOCUMENTS

JP 2001-0187136 A 7/2001
RU 2336906 C2 10/2008
RU 2437168 C2 12/2011
WO WO-96/27402 A1 9/1996
WO WO-2005/050524 A2 6/2005
WO WO-2008/017041 A2 2/2008
WO WO-2012/007942 A2 1/2012

* cited by examiner

INDUCTIVELY POWERED MODULAR MEDICAL DEVICE SYSTEM

TECHNICAL FIELD

The subject matter described herein relates to a modular medical device system. In particular, the current subject matter is directed to a system for coordinated operation of multiple medical devices such as infusion pumps and vital signs monitors.

BACKGROUND

Medical device systems may utilize a plurality of different medical devices that are distinct stand-alone or independent medical devices. For example, some conventional infusion pumping systems may include up to about four functionally distinct stand-alone infusion pumps. Conventional infusion pumps are typically stand-alone complex devices that are only able to provide independent complex infusion functions. As such, coordination or control of the devices collectively is complex and difficult. Moreover, purchasing of the complex stand-alone devices can be financially burdensome.

Further, hospitals using each of several different models of pumps, each employing distinct user interfaces, makes both learning and practicing their operation more time consuming with risk of error elevated. For instance, there may be pumps for syringe, large volume, patient controlled analgesia, anesthesia and other uses. These difficulties can be compounded when there are other medical devices being used for patient care including various types of vital sign monitors and the like.

SUMMARY

In one aspect, a system includes an inductive backplane, at least one communications interface, and a control unit. The inductive backplane is configured to secure and inductively power a plurality of detachable medical device modules. The control unit controls, via the at least one communications interface, at least one attribute of each medical device module when the medical device module is secured to the inductive backplane.

The system can include at least one optical data transceiver and a plurality of first optical data transmission ports along the inductive backplane, both coupled to the at least one communications interface. In such arrangement, the medical device module can include a second optical data transmission port positioned along an optical path with a corresponding first optical data transmission port when the medical device module is secured to the inductive backplane. The at least one optical data transceiver can be an infrared optical data transmitter. In some variations, there are a plurality of optical data transceivers and the at least one communications interface includes a communications bus coupled to each optical data transceiver.

The at least one communications interface can, in other variations, be coupled to the inductive backplane and the control unit can controls, via an induction-based communications protocol, the at least one attribute of each medical device module when the medical device module is secured to the inductive backplane.

The at least one communications interface can wirelessly and communicatively couple the control unit to at least one medical device module.

Each medical device module can have an arrangement in which it does not include an electrical galvanic connector.

A wide variety of medical device modules can be used with the current system. For example, the system can be used with infusion pumps such as syringe pumps, patient controlled infusion pumps (e.g., patient-controlled analgesia (PCA) system), large volume infusion pumps, peristaltic pumps, and the like. The medical device modules can also be one or more of a vital signs monitor, cardiac output monitors, gastric tonometers, an SpO2 sensor, an EtCO2 sensor, a blood analyte monitor, an identification module, a barcode scanner, and a radio frequency identification (RFID) scanner.

The inductive backplane can include a plurality of mounting seats, each mounting seat being configured to mechanically secure one medical device module. The mounting seats can be arranged, for example, along a vertical axis of the inductor backplane (e.g., a center line, etc.). Proximity sensors can also be included that correspond to each seat. The proximity sensors detect presence of a medical device module in the corresponding seat. The at least one communications interface can initiate communications with a medical device module in a particular seat after the corresponding proximity sensor detects the presence of the medical device module in the seat. In addition or in the alternative, the inductive backplane can commence inductive powering of a medical device module in a particular seat after the corresponding proximity sensor detects the presence of the medical device module in the seat. Furthermore, the inductive coupling between the inductive transmitter and the inductive receiver can be used to characterize proximity of the medical device module.

The at least one communications interface can be operable to receive and transmit data from at least one remote computing system via a wired and/or wireless communication link. The at least one communications interface can be operable to receive and transmit data from at least one medical device (i.e., a medical device that is not a medical device module) via a wired or wireless connection, the at least one medical device being different from the plurality of medical device modules.

The system can include an auxiliary power source for powering one or more medical device modules that are not inductively powered. In addition, the system can, in some implementations, comprise a battery for selectively powering the inductive backplane and the medical device modules.

The system can include a touch screen display extending outward from the inductive backplane. An adjustable display arm can couple the touch screen display with the inductive backplane. The adjustable display arm can be a tilt and swivel arm. In other variations, a touch screen display can be integrated into an outer surface of a housing of the system. The control unit can control the at least one attribute of one or more of the medical device modules in response to user-generated input received via the touch screen display.

The control unit can controls the at least one attribute of one or more of the medical device modules in response to data received from a remote source.

In an interrelated aspect, a system comprises an inductive backplane configured to secure and inductively power a plurality of detachable medical device modules and a display to display one or more attributes of the medical device modules when secured to the inductive backplane.

In a further interrelated aspect, a medical device module includes at least one data processor, memory storing instructions for execution by the at least one data processor, an inductive receiver for powering the at least one data processor, and a housing. The housing has a shape and size to be secured by an inductive backplane of a modular medical device system. The inductive backplane inductively powering the inductive receiver when the housing is secured thereto. The modular medical device system can also include at least one communications interface and a control unit that controls, via the at least one communications interface, at least one attribute of the medical device module when the housing is secured to the inductive backplane. In some variations, the medical device module has no external galvanic connection on an outer surface of the housing.

In still a further interrelated aspect, a medical device module can include at least one data processor, memory storing instructions for execution by the at least one data processor, a self-contained power source, a communications interface, and a housing having a shape and size to be secured by to a modular medical device system. The medical device module can operate independently when not secured to the modular medical device system and it can be controlled via the communications interface of the medical device module by the modular medical device system when the medical device module is secured to the modular medical device system.

In another interrelated aspect, an infusion pump includes at least one data processor, memory storing instructions for execution by the at least one data processor, and at least one pumping sub-system for pumping fluid passing therethrough (via a tubing set, an IV cassette, etc.). Such an infusion pump can be configured such that it does not include an external electrical galvanic connector. In some variations, the infusion pump includes an inductive receiver for being inductively powered by an inductive backplane of a modular medical device system.

In a further interrelated aspect, a modular medical device system can inductively power each of a plurality of medical device modules. Thereafter, communications are initiated between each of the medical device modules and a control unit via at least one communications interface. Subsequently, one or more attributes characterizing operation of at least one of the medical device modules are displayed on a display of the modular medical device system. In some variations, user-generated input can be received via the display (or via a different interface) that modifies at least one attribute of at least one medical device module. The control unit of the modular medical device system can them modify the at least one attribute for the at least one medical device module specified by the user-generated input.

In still another interrelated aspect, a modular medical device system can inductively power each of a plurality of medical device modules. Thereafter, communications are initiated between each of the medical device modules and a control unit via at least one communications interface. The control unit then controls one or more attributes of at least one of the medical device modules.

In some variations, data characterizing the medical device modules when secured to the inductive backplane can be provided. In this context, provided can include one or more of: displaying the provided data, storing the provided data, loading the provided data into memory, and transmitting the provided data to at least one remote computing system or medical device.

Computer program products are also described that comprise non-transitory computer readable media storing instructions, which when executed one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection (wired or peer-to-peer wireless) between one or more of the computing systems, etc.

The subject matter described herein provides many advantages. For example, the current subject matter provides enhanced usability for clinicians both with regard to the ease of coupling and decoupling medical device modules from the system and in connection with the various user interfaces provided by the system. The current subject matter also provides enhanced mobility with regard to the movement of medical device modules to be used with other inductive backplanes, with other systems, and stand-alone. Furthermore, the current subject matter is advantageous in that it enables contextual operation of medical device modules thereby increasing safety. Still further, the current subject matter is advantageous in that a clinician can scale the number of utilized medical device modules as may be required during the course of treatment for a patient. In addition, the current subject matter is advantageous in that it provides a common unified user interface which, in turn, provides enhanced usability as compared to individualized user interfaces on each type of medical device.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Figure 1:
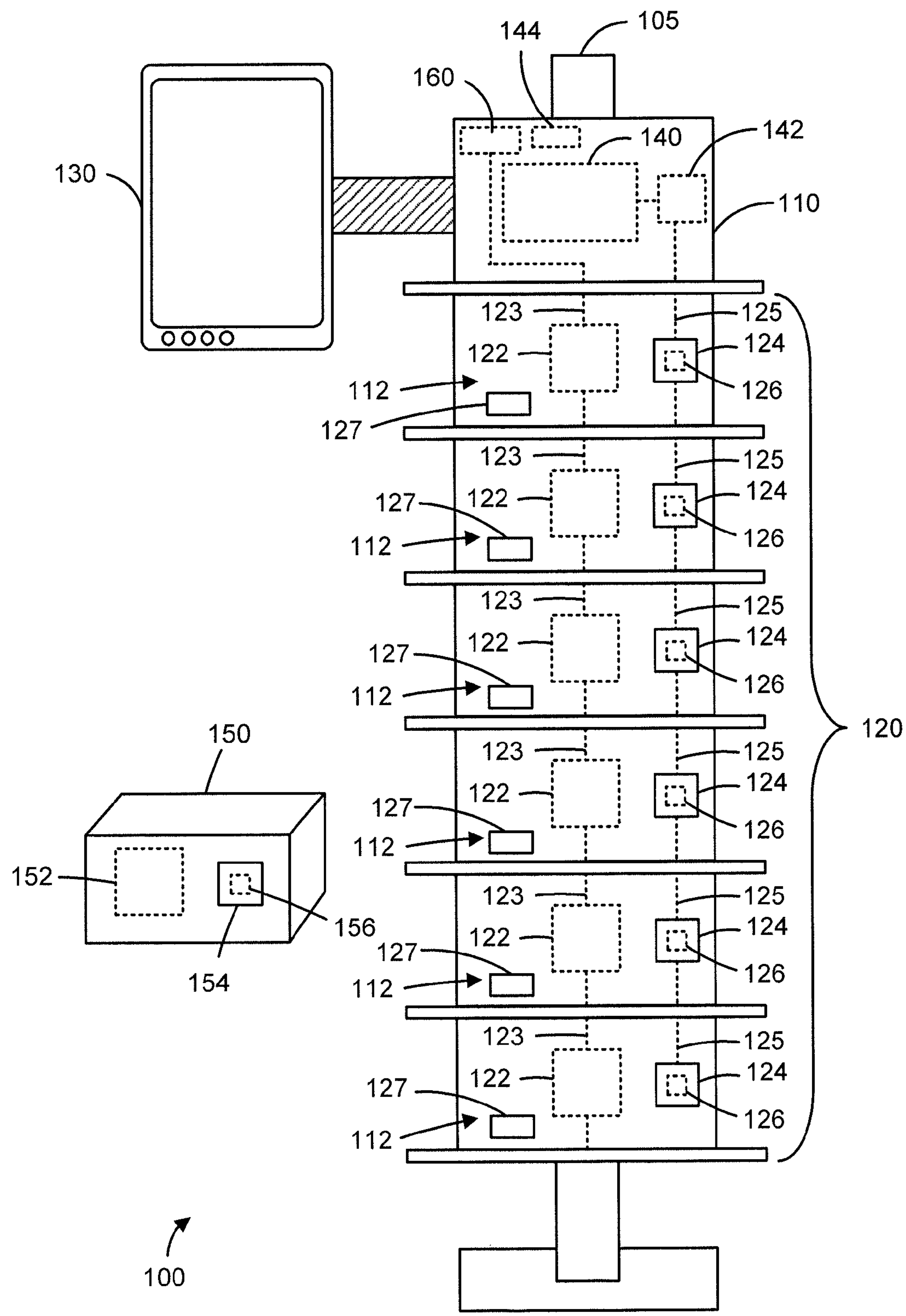
FIG. 1 is a diagram illustrating a modular medical device system.

FIG. 1 is a diagram 100 illustrating a modular medication device system 110. The system 110 comprises a backplane

120 that can be mounted on a pole 105. The backplane 120 can mechanically couple to and secure one or more medical device modules 150 along each of a series of pre-defined mounting seats 112. In some variations, each of the mounting seats 112 are uniform in size and spacing, while in other variations different sizing and/or spacing can be used to accommodate medical device modules 150 having different exterior dimensions. In addition, the mounting seats 112 can be arranged along a single axis (e.g., a vertical axis as illustrated, etc.) or they can be arranged along two or more axes. The mounting seats 112 can each have one or more mechanical elements to detachably affix the medical device modules 150 to the backplane 120.

In addition to allowing the medical device modules to be affixed to the system, the backplane 120 can provide non-contact inductive power to one or more medical device modules 150. The backplane 120 can, for each mounting location, comprise an inductive transmitter 122 for non-contact powering of a medical device module 150. A corresponding inductive receiver 152 on the medical device module 150 can, when the medical device module 150 is affixed to the mounting seat 112, be inductively coupled with inductive transmitter 122 of backplane 120. In general, energy is sent via an inductive (magnetic) coupling between inductive transmitter 122 and inductive receiver 152. As a result, there is a wireless (no galvanic contact) energy transfer between inductive backplane 120 and medical device module 150. Moreover, an electrical galvanic connector, as is typical for powering conventional medical devices, is not required to provide power to medical device module 150. Use of non-contacting energy transfer avoids metallic contacts between medical device module 150 and a power source which may be damaged, require special cleaning and pose risk of electrical heating, smoke or fire. Each inductive transmitter 122 can be coupled to an induction bus 123 which in turn is connected to a power source 160 (e.g., a wired connection to an outlet, a battery, etc.) to enable the inductive coupling of each inductive transmitter 122.

The backplane 120 can also provide an optical communications interface to one or more medical device modules 150 via respective optical communications ports 124 and optical transceivers 126 corresponding to each mounting seat 112. The medical device modules 150 can have corresponding optical communications ports 154 and optical transceiver 156 which can be optically aligned with the optical communication port 124 on the backplane 120 when the medical device module 150 is affixed to the backplane 120 so that a bi-directional data feed can be established between the optical transceivers 126, 156. Such data can relate to a variety of aspects including, but not limited to, data characterizing operation of the medical device module 150, data for controlling (e.g., modifying, monitoring, etc.) one more attributes of the medical device module 150 (e.g., software updates, configuration updates, asset locations, status information, historical data, patient information, patient treatment parameters, medication administration information, etc.), and the like. Stated differently, the data exchanged via the optical transceivers 126, 156 can comprise any data generated or otherwise used by a medical device module 150 or a caregiver using same. The data transmitted to the backplane 120 can be consumed locally by the system 110 and/or it can be transmitted to one or more remote systems/devices coupled to the system 110 via a wired or wireless communications link. The optical data transceivers 126, 156 can be infrared (IR) data transceivers such that optical data 146 is propagated by IR light as the transmission medium. The optical data transceivers can be coupled to a communications bus 125 that in turn is coupled to a communications interface 142. The communications interface 142 can, in turn, be coupled to the control unit 140. In addition or in the alternative, a second communications interface 144 can provide an outward interface for the modular medical device system 110 that provides a wired or wireless connection to other devices and/or networks. It will be appreciated that any number of communications interfaces can be used, including one communications interface for each optical data transceiver 126/seat 112.

The control unit 140 can be hardware, software, or a combination of both. For example, the control unit 140 can be a specially designed hardware module including at least one data and memory with specialized software used to control any aspect of a medical device module 150 coupled to the system 110. In other cases, the control unit 140 can be a software module (or series of modules) used to control any aspect of a medical device module 150 coupled to the system 110. As used herein, unless otherwise specified, the term control shall relate to any type of data exchange with a medical device module 150 by the control unit 140 including data generated by a medical device module 150 and data used by a medical device module 150 (software updates, power state changes, etc.). For example, the control unit 140 can be used to selectively wake up medical device modules 150 coupled to the inductive backplane 120 from a sleep state. Furthermore, the control unit 140 can be coupled to one or more remote computing systems (via the communications interface 144) to allow for the remote control of the medical device modules 150.

Each mounting seat 112 can include a shelf with dove tail features extending from a housing of the system 110. Each medical device module 150 can include a latch mechanism on a top rear edge that affixes to the housing of the system 110. The latch mechanism can reduce load on the shelf and can cause the medical device module 150 to rotate back into contact with the system 110 under load (rather than deflect away from it). This arrangement can help insure that the inductive transmitter 122 is positioned properly and secured in relation to the inductive receiver 152.

Each mounting seat 112 can include a proximity sensor 127 that can detect the presence of a medical device module 150. The proximity sensors 127 can be optical, electric, electro-mechanical, and/or mechanical devices. For example, the proximity sensors 127 can comprise a Hall effect sensor and/or a mechanical switch. The presence of a medical device module 150 can be used to initiate, for example, inductive powering by the corresponding inductive transmitter 122 and/or communications via the communications interface 142. The proximity sensor 127 can also indicate an alarm condition when a medical device module 150 is not completely secured so that appropriate actions can be taken.

Medical device module 150 can be any medical device that is compatible for scalability in a modular medical device system. For instance, the modular medical device system 110 can utilize one or more medical device modules 150 depending on the functionality that is needed for proper care of a patient. Moreover, a modular medical device system 110 can be scaled up to incorporate additional medical device modules 150 and also scaled down by removing medical device modules 150.

For example, if patient care requires only one infusion pump, then the modular medical device system 110 can include a single affixed infusion pump. Moreover, if patient care requires two infusion pumps, then the modular medical device system 110 can be scaled up to include an affixed additional infusion pump.

Medical device modules 150 can include, but is not limited to, an infusion pump (e.g., a large volume pump (LVP), a syringe pump), a patient-controlled analgesia (PCA) system, a vital signs monitor (VSM) (e.g., an SpO2 sensor, an EtCO2 sensors, cardiac output monitors, gastric tonometers, etc.), a bedside blood analyte analyzer (e.g. blood glucose), an Auto-ID module (barcode scanner and RFID), and other devices which measure physiological parameters associated with a patient and/or assist with the clinical care of the patient (and such medical device modules 150 may not necessarily measure physiological parameters of the patient).

Modular medical device system 110 can also comprise a display unit 130 that provides a unified interface that characterizes the operation of various medical device modules 150 coupled to the backplane 120. The display unit 130 can comprise a touch screen interface that allows a user to selectively view and alter performance parameters/metrics of individual medical device modules 150, concurrently view performance parameters/metrics of multiple medical device modules 150, and additionally orchestrate complex sequences of infusions/operations from multiple medical device modules 150. The display unit 130 can be affixed to an outer housing of the modular medical device system 130/inductive backplane 120 by a tilt and swivel arm mount that allows the display unit to be moved on different sides of the system 110 and/or to change varying positions (to accommodate different positions/heights of caregivers).

The display unit 130 can include a speaker to provide audio cues relating to various aspects of medical device modules 150 (in other versions the speaker is located elsewhere in the system 110). When the medical device modules 150 are coupled to the backplane 120, audio cues such as alarms for such medical device modules 150 can be delegated so that the system 110 handles the alarms whether via an audio and/or visual cue in the display unit 130 or by an audio cue generated elsewhere in the system 110. In some cases, some alarms can be still be handled by a medical device module 150 while other alarms are handled by the system 110.

Figure 2:
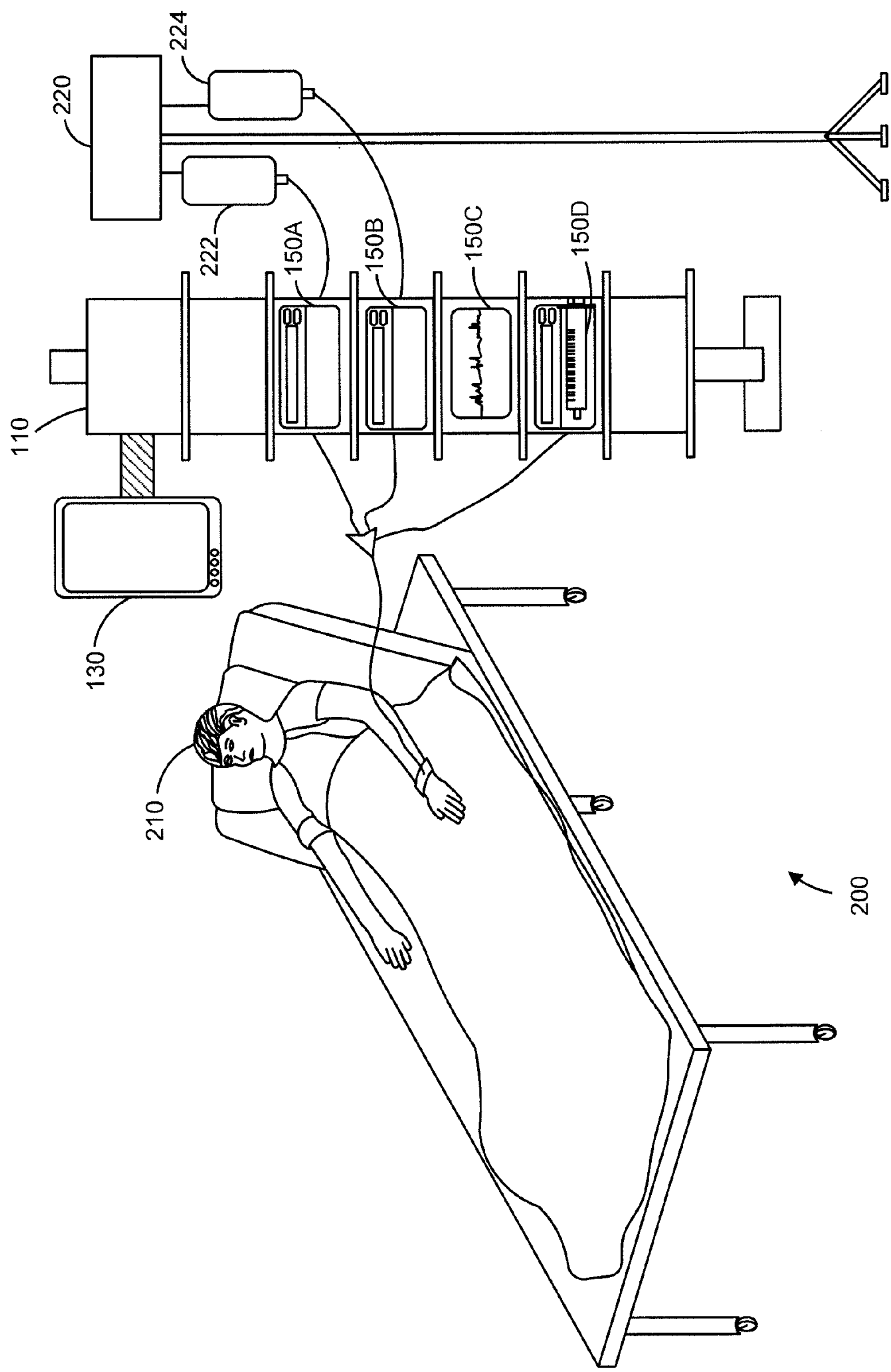
FIG. 2 is a diagram illustrating a modular medical device system in a clinical setting.

FIG. 2 is a diagram 200 illustrating a modular medical device system 110 in a clinical setting. In particular, in this view, the modular medical device system 110 is coupled to two infusion pumps 150A, 150B, a vital signs monitor 150C, and a syringe pump 150D. The infusion pumps 150A and 150B are respectively fluidically coupled to two fluid/medication containers 222, 224 suspended from an IV pole 220. In addition, each of the infusion pumps 150A and 150B and the syringe pump 150D are fluidically coupled to an IV catheter inserted into a patient 210 so that the corresponding fluids can be delivered to the patient. The modular medical device system 110 monitors and/or controls how fluids from the respective sources 150A, 150B, 150D are delivered to the patient 210. It will be appreciated that varying numbers of medical device modules 150 can be utilized depending on the particular condition of and/or treatment the patient 210.

Figure 3:
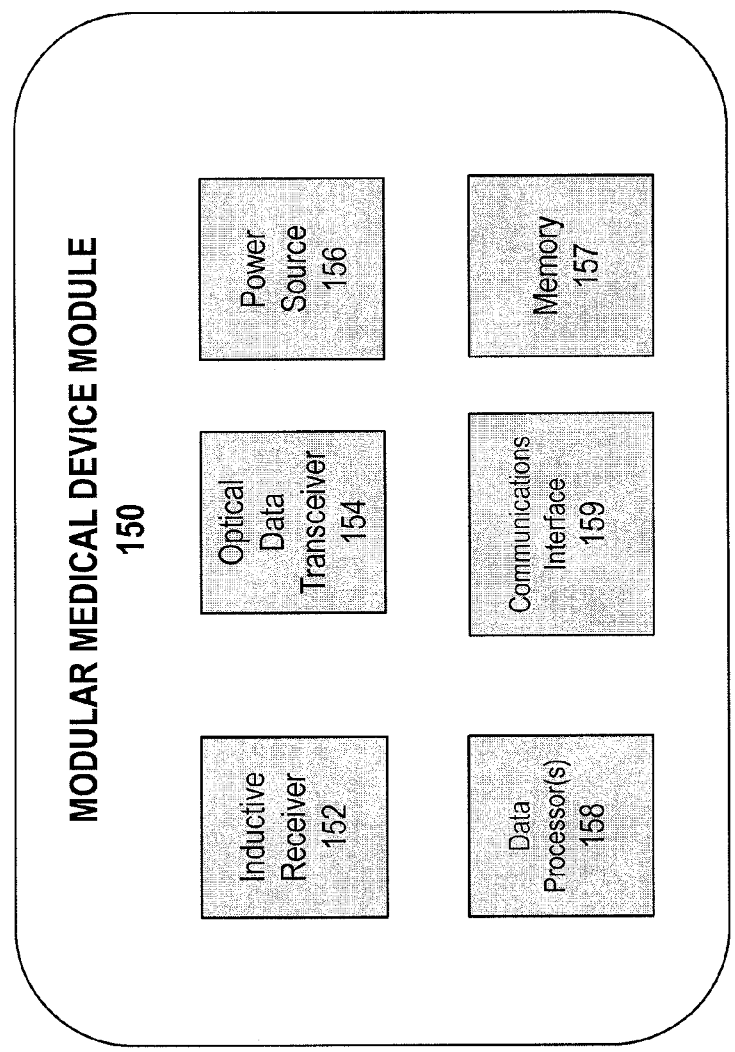
FIG. 3 is a logic diagram illustrating a medical device module.

FIG. 3 is a logic diagram 300 of a medical device module 150. With FIG. 3, each medical device module 150 can include a secondary power source 156 such as a battery or a wired connection to an external power source. For example, the secondary power source 156 can power medical device module 120 when inductive receiver 152 is unable to power medical device module 150. In one scenario, medical device module 150 is an infusion pump that is associated with (and fluidly communicating with) a patient. If the patient is moved to another location (e.g., to an x-ray room which is away from inductive backplane 110), then medical device module 150 must also move with the patient away from inductive backplane 120 in order to continue the current infusion without interruption. Upon a certain distance from inductive backplane 120, inductive receiver 152 cannot be energized by inductive backplane 120 and therefore cannot power medical device module 150. In other cases, the inductive backplane 120 may be turned off or operating in a mode not allowing the inductive receiver 152 to be energized. Accordingly, power source 156 (which may also be charged through inductive receiver 152) is able to provide the requisite power for medical device module 150. In one variation, the power source 156 is a battery that can keep medical device module 150 operational in a range of about two to four hours.

Each medical device module 150 can also include memory 157 and at least one data processor 158. The memory 157 can store instructions for execution by the at least one data processor 158 for use, for example, in the operation of the medical device module in a clinical setting. The memory 157 can also store data relating to the operation of the medical device module such as data characterizing how the medical device module 150 is used and parameters relating to same (e.g., number of hours operated, thresholds for alerts, etc.), performance and status information, and well as other aspects relating to the use of such medical device module 150 such as patient data, medication administration data, patient treatment parameters, etc. It is noted that when a medical device module 150 is reattached to the prior inductive backplane or a different inductive backplane, information required to continue the infusion stored in memory 157, without interruption, can be transmitted from the medical device module 150 to the backplane (and to the control unit 140).

Each medical device module 150 can also comprise an additional communications interface 159 other than the optical data transceiver 154 (in some variations the optical data transceiver 154 may not form part of the medical device module 150 and so the communications interface 159 may be the only gateway for communication outside of the medical device module 150). This communications interface 159 can be fixed and/or wireless and be used to communicate to computer networks and peer-to-peer pairing with other devices when the medical device module 150 is not coupled to the backplane 120.

In some implementations, the communications interface 159 can be used in addition or instead of the optical data transceiver 154 when the medical device module 150 is coupled to the backplane 120. For example, the medical device module 150 can be seated on the backplane 120 but not have an optical data transceiver. In such a scenario, the communications interface 159 can wirelessly communicate with the control unit 140 of the modular medical device system 110 so that the operation of the medical device module 150 can be monitored and/or controlled by the modular medical device system 110 (whether or not the medical device module 150 is seated). Various types of wireless communications can be used (for this and other aspects described herein) such as short distance protocols such as BLUETOOTH, near field communication (NFC), WiFi, ZIGBEE, and the like.

As noted above, the system 110 comprises a control unit 140 (which in turn can comprise at least one data processor and memory for storing instructions for execution by the at least one data processor and/or data characterizing or otherwise relating to the operation of medication device modules 150). The control unit 140 can act to individually monitor and/or control the operation of the medical device modules 150 affixed to the backplane 120 such that the functionality of the medical device modules 150, alone and/or in combination are increased. In some cases, the control unit 140 can orchestrate the operation of multiple medical device modules 150. For example, certain sequences of operation and/or concurrent operation can be defined amongst the medical device modules 150. Such an arrangement can permit, for example, coordinated infusion from different fluid sources. Some medical device modules 150 can have the ability to function fully independent of the control unit 140 for the purpose of basic operations. However, the modules acquire more complex abilities and functionality when operating under the command and coordination of the controller.

Figure 4:
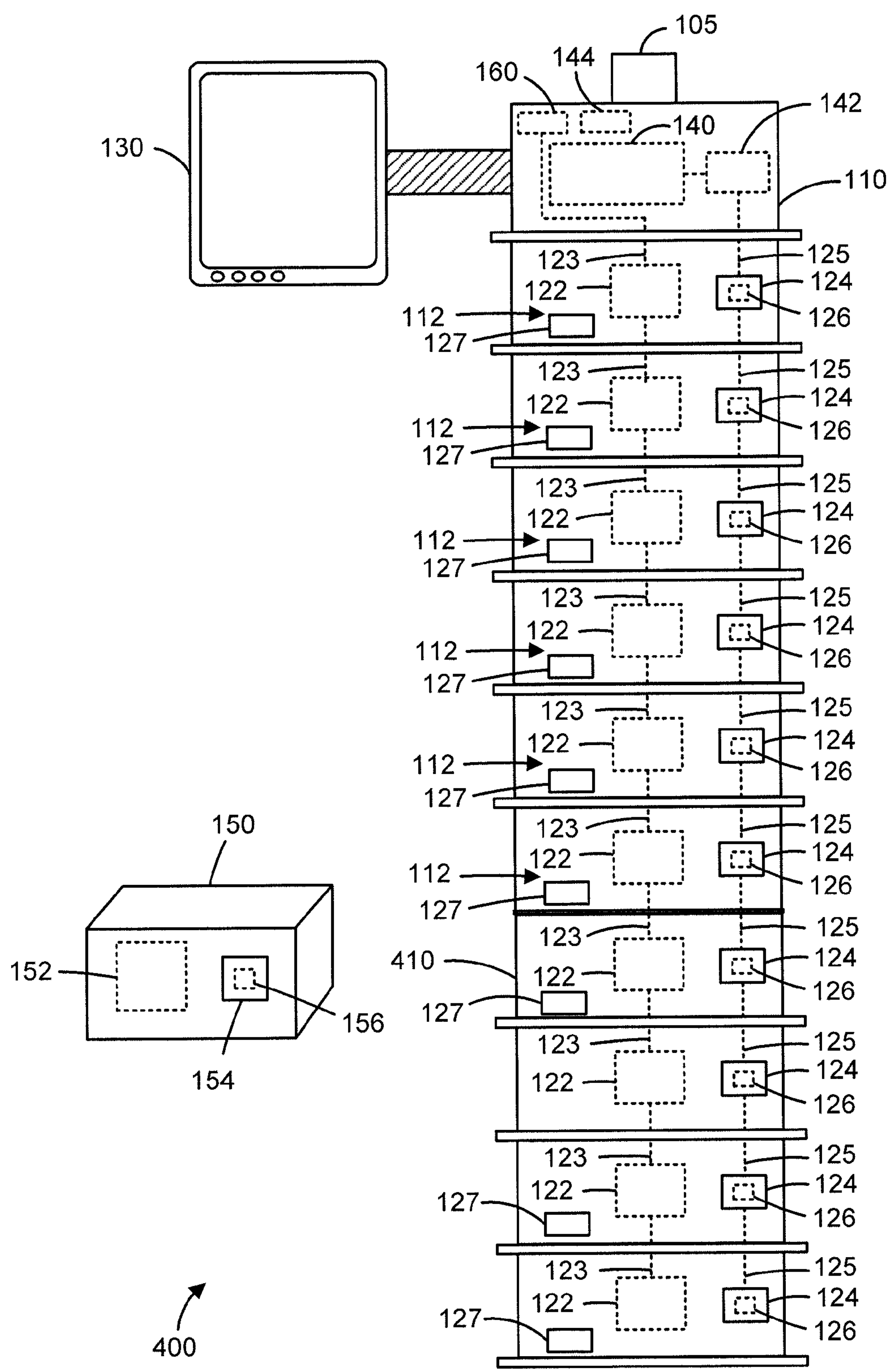
FIG. 4 is a diagram illustrating a modular medical device system with a backplane extension.

FIG. 4 is a diagram 400 that illustrates a backplane extension 410. The backplane extension 410 provides additional seats 112 to which medical device modules 150 can be coupled. The backplane extension 410 can be coupled physically and/or electrically to the system 110 so that any medical device modules 150 coupled to the backplane extension 410 can be coupled to the control unit 140 and function in a similar manner to the medical device modules 150 coupled to the backplane 120. Stated differently, backplane extension 410 can function similarly to the inductive backplane 120. It will be appreciated that the backplane 120 and the backplane extension 410 can each be configured to seat any number of medical device modules 150 as may be desired.

In some clinical settings, multiple backplane extensions 410 and/or backplanes 120 can be utilized to serve a single patient. With such an arrangement, each inductive backplane 120 and backplane extension 410 can have local communication with the other inductive backplanes 120, 410 serving the same patient to provide coordination of functionality and data. The communication can be wired and/or wireless using, for example, short range digital radio technology, WiFi, optical data transceivers, BLUETOOTH, ZIGBEE, NFC, and the like.

Figure 5:
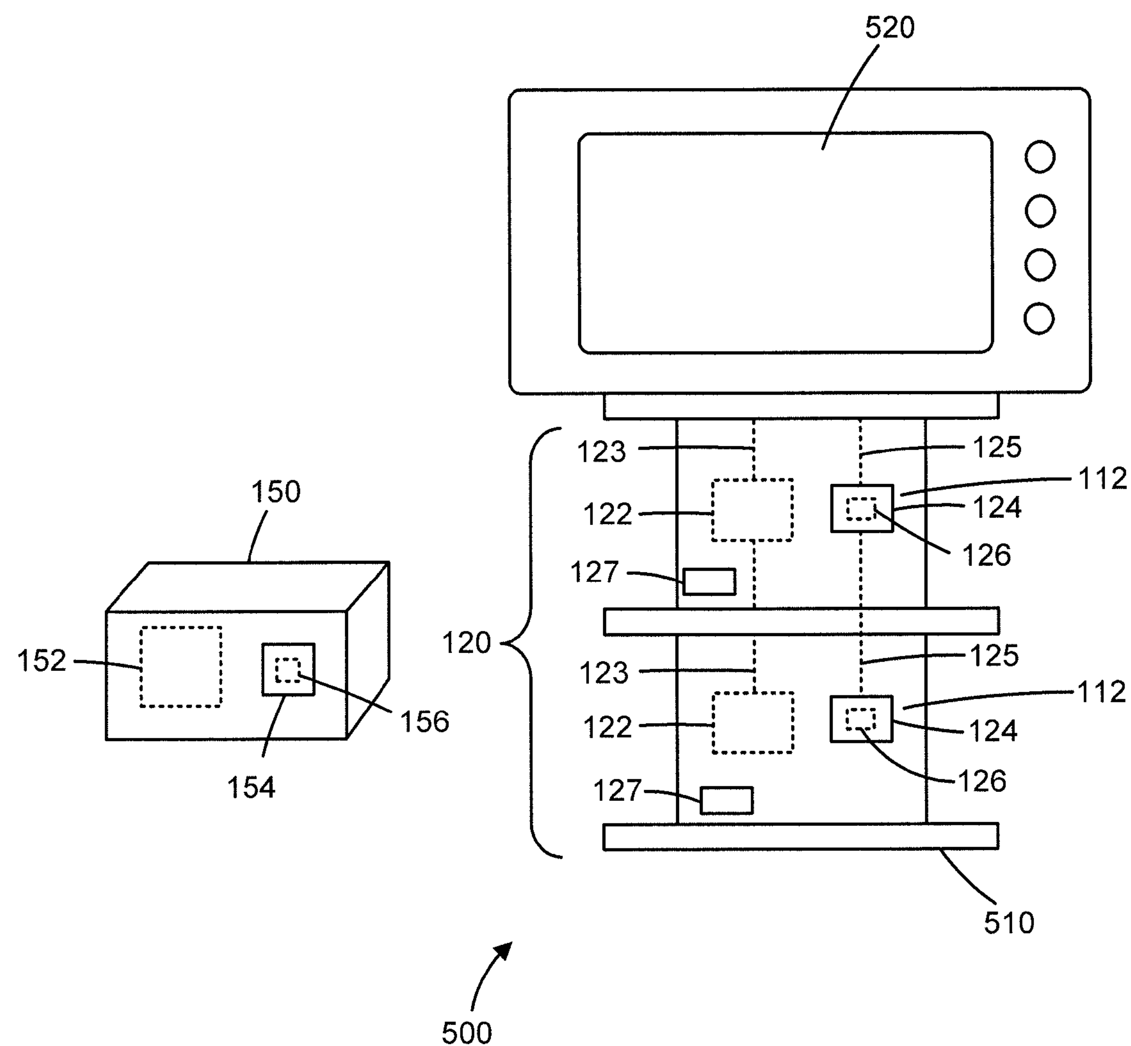
FIG. 5 is a diagram illustrating a compact modular medical device system.

FIG. 5 is a diagram 500 that illustrates a variation of a modular medical device system 510 that is more compact. This modular medical device system 120 can, for example, include fewer seats 112 to which medical device modules 150 can be affixed, than the modular medical device system 110 (illustrated in FIG. 1) to allow it to sit on a table top or other flat surface. In addition, the display 520 can be placed immediately above the medical device modules 150 to further decrease the footprint of the modular medical device system 520.

Figure 6:
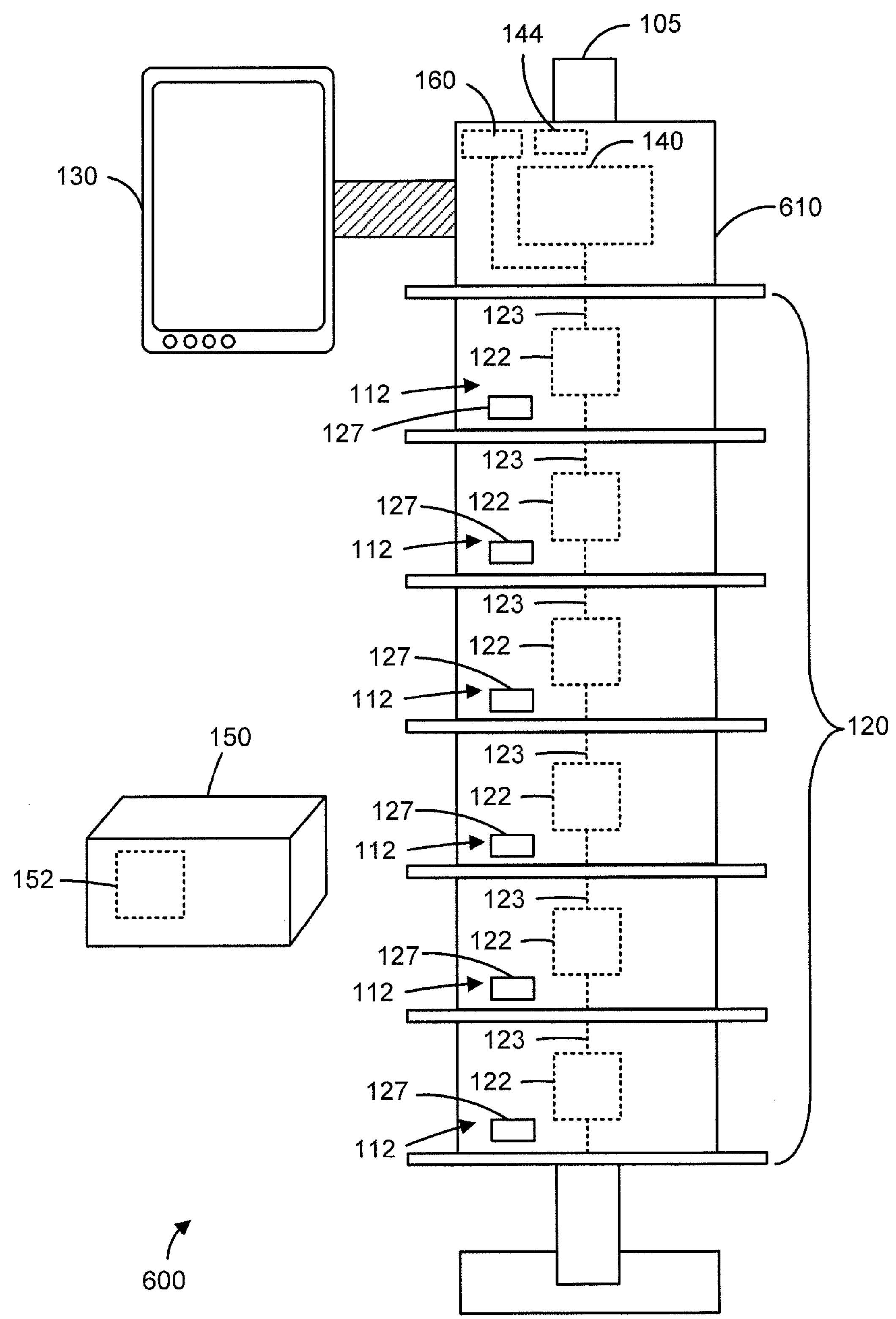
FIG. 6 is a diagram illustrating a modular medical device system without an optical communications sub-system.
Figure 7:
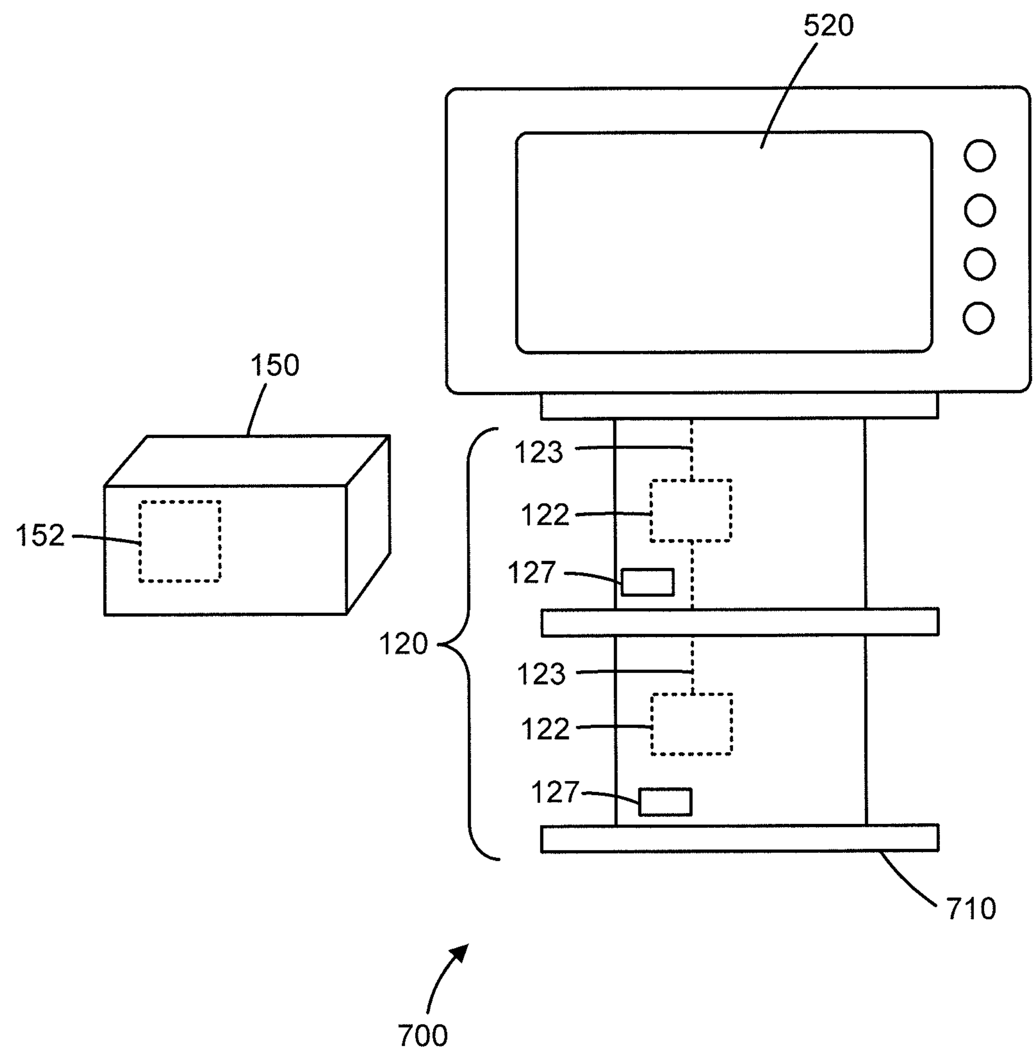
FIG. 7 is a diagram illustrating a compact modular medical device system without an optical communications sub-system.

FIG. 6 is a diagram 600 of a modular medical device system 610 and FIG. 7 is a diagram 700 of a compact modular medical device system 710 that respectively illustrate alternative implementations to the modular medical device system 110 of FIG. 1 and the compact modular medical device system 510 of FIG. 5. With both of these variations, communications with medical device modules 150 are effected using a communications protocol different from the optical sub-systems (124, 125, 126, 142). For example, in some variations, the inductive transmitters 122 and inductive bus 123 can be used to exchange data with the inductive receiver 152 to effect a near field magnetic induction communication system. Such an arrangement can provide a short range wireless physical layer that communicates by coupling a tight, low-power, non-propagating magnetic field between the inductive transmitter 122 and the inductive receiver 152. The transmitter coil in the inductive transmitter 122 can modulate a magnetic field which is measured by the inductive receiver 152 in another device. It will be appreciated that the communications are bi-directional and as such, the inductive receiver 152 can also transmit data to the inductive transmitter 122.

In other variations, the modular medical device systems 610, 710 can communicate and exchange data with the medical device modules 150 via a wireless communications protocol including, but not limited to short range digital radio technology, WiFi, optical data transceivers, BLUETOOTH, ZIGBEE, NFC, and the like.

Figure 8:
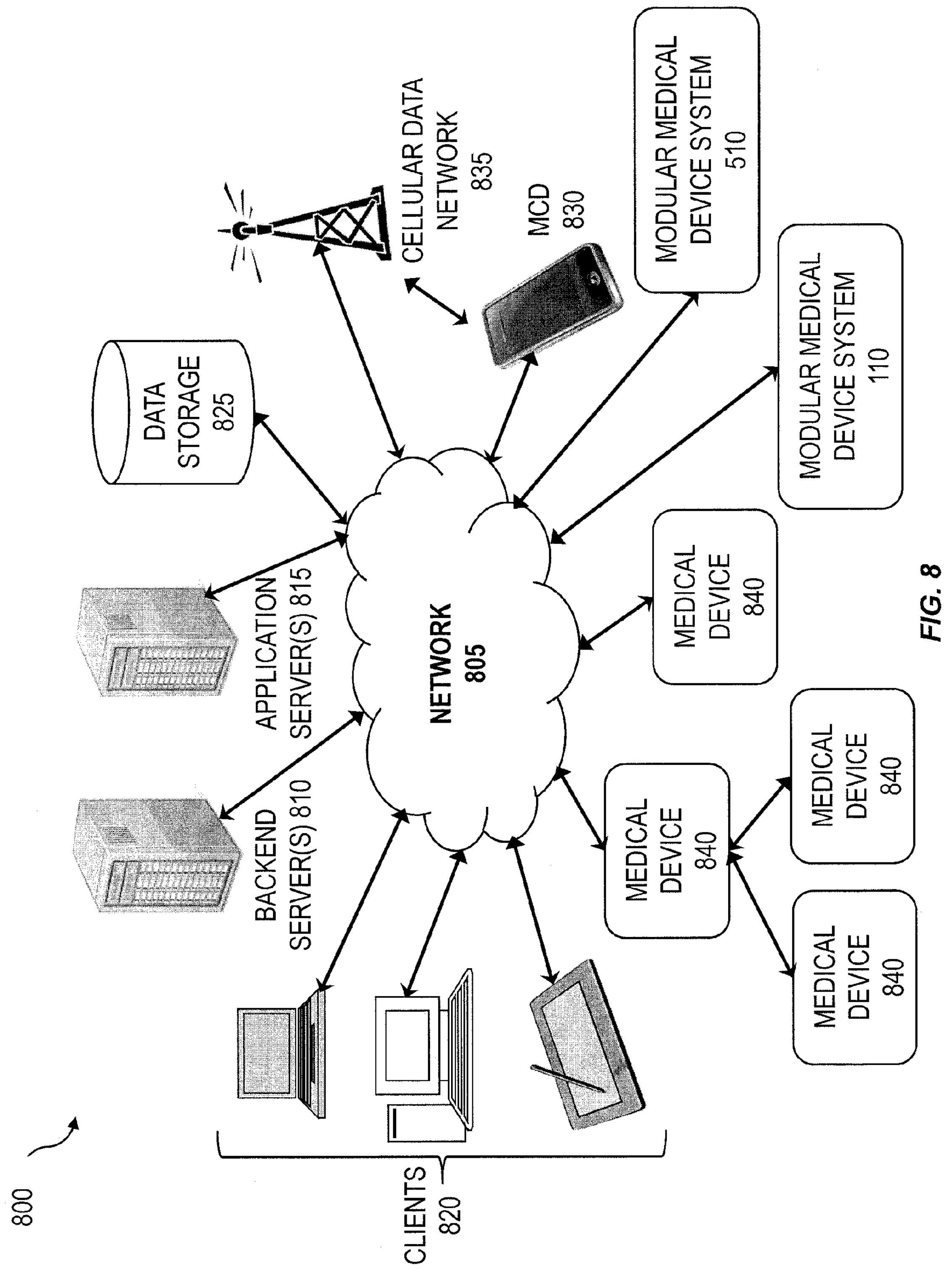
FIG. 8 is a diagram illustrating a computing landscape including a modular medical device system.

FIG. 8 is a system diagram illustrating a computing landscape 800 within a healthcare environment such as a hospital that includes modular medical device systems 110, 510. Various devices and systems, both local to the healthcare environment and remote from the healthcare environment, can interact via at least one computing network 805. This computing network 805 can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

The modular medical device systems 110, 150 can include at least one communications interface that can access the computing network 805 either via a fixed wired connection or via a wireless connection (via, for example, one or more access points). In addition, the modular medical device systems 110, 150 can also couple to other components within the computing landscape 800 via direct wired or wireless peer-to-peer coupling (not shown). Furthermore, in some cases, one or more of the modular medical device systems 110, 510 can be self-contained and is not connected to any other devices or networks. The modular medical device systems 110, 510 can transmit data via the computing network 805 to any of the other components within the landscape 800 that characterizes the medical device modules 150. In addition, the modular medical device systems 110, 510 can receive data from the computing network 805 relating to monitoring and in some cases controlling one or more attributes of the medical device modules 150 (e.g., software updates, configuration updates, historical data, status information, assets location, patient information, etc.).

In particular, aspects of the computing landscape 800 can be implemented in a computing system that includes a back-end component (e.g., as a data server 810), or that includes a middleware component (e.g., an application server 815), or that includes a front-end component (e.g., a client computer 820 having a graphical user interface or a Web browser through which a user may interact with an implementation of the subject matter described herein), or any combination of such back-end, middleware, or front-end components. A client 820 and server 810, 815 are generally remote from each other and typically interact through the communications network 805. The relationship of the clients 820 and servers 810, 815 arises by virtue of computer programs running on the respective computers and having a client-server relationship to each other. Clients 820 can be any of a variety of computing platforms that include local applications for providing various functionality within the healthcare environment. Example clients 820 include, but are not limited to, desktop computers, laptop computers, tablets, and other computers with touch-screen interfaces. The local applications can be self-contained in that they do not require network connectivity and/or they can interact with one or more of the servers 810, 815 (e.g., a web browser).

A variety of applications can be executed on the various devices and systems within the computing landscape such as electronic health record applications, medical device monitoring, operation, and maintenance applications, scheduling applications, billing applications and the like. As another example, the applications can comprise a collection of enterprise-based applications that provide dose error reduction software (DERS) for the modular medical device systems 110, 150 incorporates a role-based view of infusion data, provides a comprehensive platform for connectivity to external hospital applications, and enables directed maintenance and calibration activities for devices, storage of clinical and device history, etc. As a further example, the applications can provide for remote alarms management and/or asset tracking for medical device modules 150 coupled to one or more of the modular medical device systems 110, 150.

The network 805 can be coupled to one or more data storage systems 825. The data storage systems 825 can include databases providing physical data storage within the healthcare environment or within a dedicated facility. In addition, or in the alternative, the data storage systems 825 can include cloud-based systems providing remote storage of data in, for example, a multi-tenant computing environment. The data storage systems 825 can also comprise non-transitory computer readable media.

Mobile communications devices (MCDs) 830 can also form part of the computing landscape 800. The MCDs 830 can communicate directly via the network 805 and/or they can communicate with the network 805 via an intermediate network such as a cellular data network. Various types of communication protocols can be used by the MCDs 830 including, for example, messaging protocols such as SMS and MMS. In some cases, the MCDs 830 can receive alerts generated from the operation of the medical device modules 150 coupled to the backplane 120 and/or they can otherwise be used to monitor the operation of such medical device modules 150.

Various types of medical devices 840 can be used as part of the computing landscape 800. These medical devices 840 can comprise, unless otherwise specified, any type of device or system with a communications interface that characterizes one or more physiological measurements of a patient and/or that characterize or are used for the treatment of a patient. In some cases, the medical devices 840 communicate via peer to peer wired or wireless communications with another medical device 840 (as opposed to communicating with the network 805). For example, the medical device 840 can comprise a bedside vital signs monitor that is connected to other medical devices 840 (and/or the modular medical device system 110, 510), namely a wireless pulse oximeter and to a wired blood pressure monitor. One or more attributes of the medical devices 840 can be locally controlled by a clinician, controlled via a clinician via the network 805, and/or they can be controlled by one or more of a server 810, 815, a client 620, a MCD 830, and/or another medical device 840 or the modular medical device systems 110, 510.

The computing landscape 800 can provide various types of functionality as may be required within a healthcare environment such as a hospital. For example, a pharmacy can initiate a prescription via one of the client computers 820. This prescription can be stored in the data storage 825 and/or pushed out to other clients 820, an MCD 830, and/or one or more of the medical devices 840 and/or one of the medical device modules 150 forming part of the modular medical device system 110. In addition, the medical devices 840 and the modular medical device system 110 can provide data characterizing one or more physiological measurements of a patient and/or treatment of a patient (e.g., medical device 840 can be an infusion management system, etc.). The data generated by the modular medical device system 110 and the medical devices 840 can be communicated to other medical devices 840, the servers 810, 815, the clients 820, the MCDs 830, and/or stored in the data storage systems 825.

Figure 9:
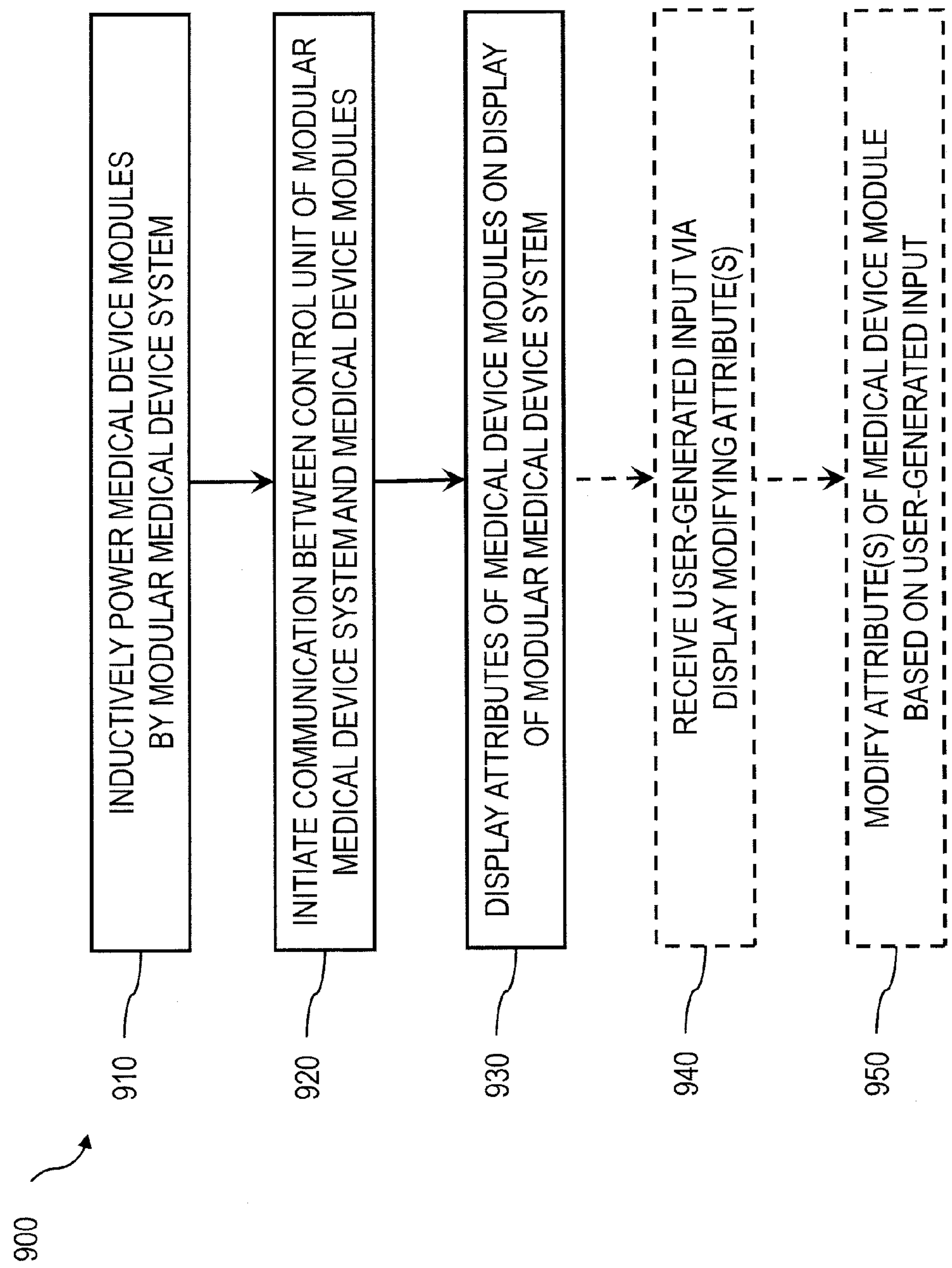
FIG. 9 is a first process flow diagram illustrating a method of operation of a modular medical device system.

Various methods can be implemented in accordance with the current subject matter. FIG. 9 is a process flow diagram 900 illustrating a method in which, at 910, a modular medical device system inductively powers each of a plurality of medical device modules. The modular medical device system includes an inductive backplane configured to secure and inductively power the plurality of medical device modules, a communications interface, a display, and a control unit. The control unit can control at least one attribute of each medical device module via the communications interface when the medical device module is secured to the inductive backplane. Thereafter, at 920, communications are initiated between each of the medical device modules and the control unit via the communications interface. The display, at 930, then displays one or more attributes characterizing operation of at least one of the medical device modules. In addition, optionally, at 940, user-generated input modifying at least one attribute of at least one medical device module is receiving via the display of the modular medical device system. As a result, at 950, the control unit modifies the at least one attribute for the at least one medical device module as specified by the user-generated input. In other scenarios, one or more attributes of the medical device modules can be modified from a component/source remote from the modular medical device system.

Figure 10:
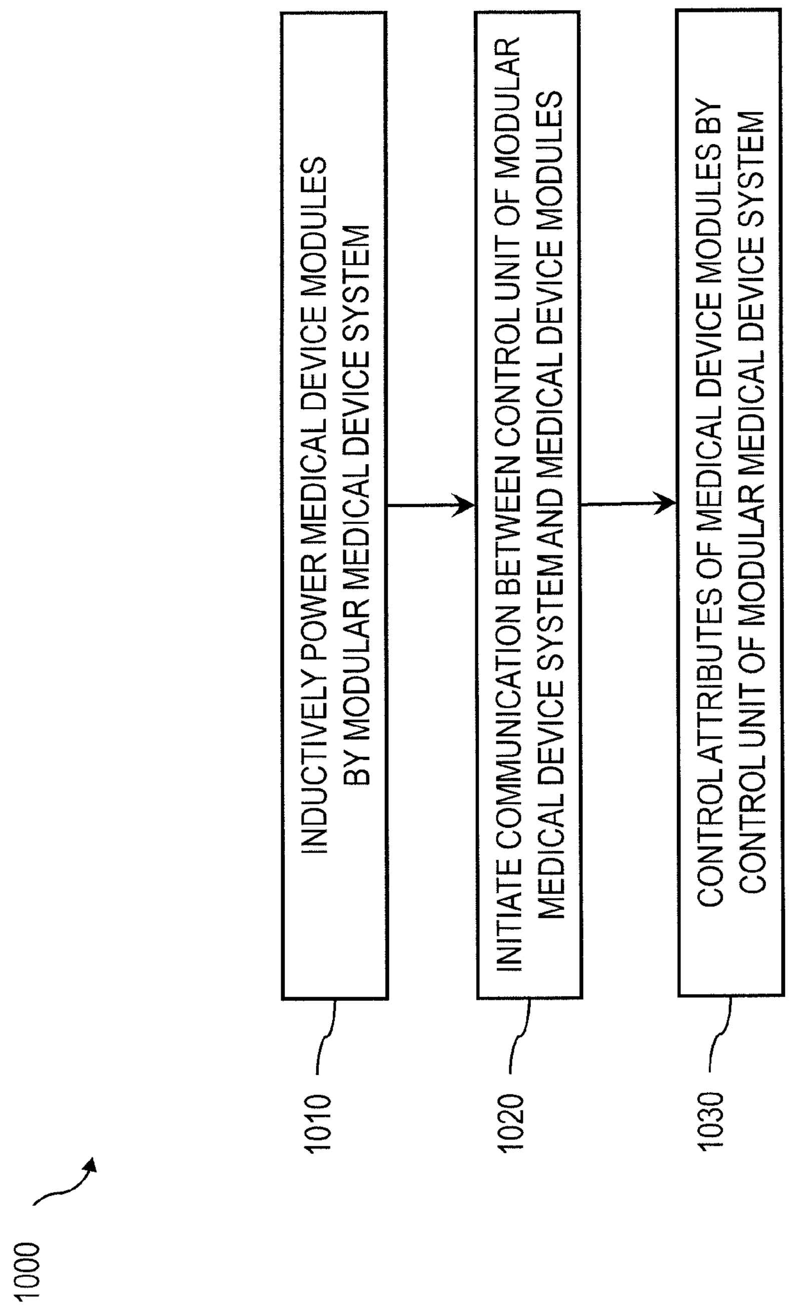
FIG. 10 is a second process flow diagram illustrating a method of operation of a modular medical device system.

FIG. 10 is a process flow diagram 1000 illustrating a method in which, at 1010, a modular medical device system inductively powers each of a plurality of medical device modules. The modular medical device system includes an inductive backplane configured to secure and inductively power the plurality of medical device modules, a communications interface, a display, and a control unit. The control unit can control at least one attribute of each medical device module via the communications interface when the medical device module is secured to the inductive backplane. Thereafter, at 1020, communications is initiated between each of the medical device modules and the control unit via the at least one communications interface. One or more attributes of at least one of the medical device modules are then, at 1030, controlled by the control unit.

The following U.S. patent applications each filed on Mar. 14, 2013 describe infusion pumps and infusion pump mechanisms that can be used in connection with the current subject matter and are all hereby incorporated by reference in their entirety: U.S. patent application Ser. No. 13/827,775 entitled “Pump Segment Placement”; U.S. patent application Ser. No. 13/827,036 entitled “Memory and Identification Associated With IV Set”; U.S. patent application Ser. No. 13/828,777 entitled “Cooperation of Platen and Pump Cassette for Pump Device”; U.S. patent application Ser. No. 13/829,425 entitled “Rotary Valve for a Disposable Infusion Set”; U.S. patent application Ser. No. 13/829,854 entitled “Infusion Pump Configured to Engage a Sensor With Tubing"; and U.S. patent application Ser. No. 13/830,175 entitled "IV System to Assist With Line Management".

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), the Internet, WiFI (IEEE 802.11 standards), NFC, BLUETOOTH, ZIGBEE, and the like.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A system comprising:

an inductive backplane configured to secure and inductively power a plurality of detachable medical device modules, the inductive backplane including a plurality of mounting seats, each mounting seat being configured to mechanically secure to a medical device module;

a dedicated inductive transmitter positioned at each of the mounting seats of the inductive backplane, each dedicated inductive transmitter adapted to couple to a corresponding inductive receiver of a corresponding medical device module when the corresponding medical device module is positioned on the mounting seat such that the inductive backplane provides non-contact, inductive power to the corresponding medical device module via a coupling between the inductive transmitter and the corresponding inductive receiver of the corresponding medical device module;

at least one communications interface located at each of the mounting seats; and a control unit to control, via the at least one communications interface, an infusion attribute of each medical device module when the medical device module is secured to the inductive backplane.

2. A system as in claim 1, further comprising:

at least one optical data transceiver coupled to the at least one communications interface; and a plurality of first optical data transmission ports along the inductive backplane coupled to the at least one communications interface;

wherein each medical device module comprises a second optical data transmission port positioned along an optical path with a corresponding first optical data transmission port when the medical device module is secured to the inductive backplane.

3. A system as in claim 2, wherein the at least one optical data transceiver is an infrared optical data transmitter.

4. A system as in claim 1, wherein there are a plurality of optical data transceivers and the at least one communications interface comprises a communications bus coupled to each optical data transceiver.

5. A system as in claim 1, wherein there are a plurality of optical data transceivers and a plurality of communications interfaces that each correspond to a different optical data transceiver.

6. A system as in claim 1, wherein the at least one communications interface is coupled to the inductive backplane and the control unit controls, via an induction-based communications protocol, the infusion attribute of each medical device module when the medical device module is secured to the inductive backplane.

7. A system as in claim 1, wherein the at least one communications interface wirelessly couples the control unit to at least one medical device module.

8. A system as in claim 1, wherein each medical device module does not comprise an electrical galvanic connector.

9. A system as in claim 1, wherein the plurality of medical device modules comprise at least one fluid infusion pump.

10. A system as in claim 9, wherein the at least one fluid infusion pump is selected from a group consisting of: syringe pumps, patient controlled infusion pumps, large volume infusion pumps, and peristaltic pumps.

11. A system as in claim 1, wherein the plurality of medical device modules comprise a patient-controlled analgesia (PCA) system.

12. A system as in claim 1, wherein the plurality of medical device modules comprises at least one of: a vital signs monitor, a blood analyte monitor, cardiac output monitors, gastric tonometers, an SpO2 sensor, an EtCO2 sensor, an identification module, a barcode scanner, and a radio frequency identification (RFID) scanner.

13. A system as in claim 1, wherein the plurality of mounting seats are arranged along a vertical axis of the inductor backplane.

14. A system as in claim 1, further comprising a proximity sensor corresponding to each seat, the proximity sensor detecting presence of a medical device module in the corresponding seat.

15. A system as in claim 14, wherein the at least one communications interface initiates communications with a medical device module in a particular seat after the corresponding proximity sensor detects the presence of the medical device module in the seat.

16. A system as in claim 14, wherein the inductive backplane commences inductive powering of a medical device module in a particular seat after the corresponding proximity sensor detects the presence of the medical device module in the seat.

17. A system as in claim 1, wherein the at least one communications interface operable to receive and transmit data from at least one remote computing system.

18. A system as in claim 1, wherein the at least one communications interface is operable to receive and transmit data from at least one medical device via a wired or wireless connection, the at least one medical device being different from the plurality of medical device modules.

19. A system as in claim 1, further comprising: an auxiliary power source for powering one or more medical device modules that are not inductively powered.

20. A system as in claim 1, further comprising: a battery for selectively powering the inductive backplane and the medical device modules.

21. A system as in claim 1, further comprising: a touch screen display.

22. A system as in claim 21, further comprising: an adjustable display arm coupling the touch screen display with the inductive backplane.

23. A system as in claim 22, wherein the adjustable display arm is a tilt and swivel arm.

24. A system as in claim 21, further comprising:

a housing enveloping the inductive backplane;

wherein the touch screen display is integrated into an outer surface of the housing.

25. A system as in claim 21, wherein the control unit controls the infusion attribute of one or more of the medical device modules in response to user-generated input received via the touch screen display.

26. A system as in claim 1, wherein the control unit controls the infusion attribute of one or more of the medical device modules in response to data received from a remote source.

* * * * *